United States Patent [19]
Dennis

[11] Patent Number: 5,853,392
[45] Date of Patent: Dec. 29, 1998

[54] SLEEVE TROCAR WITH PENETRATION INDICATOR

[76] Inventor: William G. Dennis, 11222 St. Johns Industrial Pkwy., Jacksonville, Fla. 32246

[21] Appl. No.: 832,294

[22] Filed: Apr. 3, 1997

[51] Int. Cl.⁶ ..................................................... A61M 5/178
[52] U.S. Cl. .......................... 604/164; 604/158; 604/118; 606/167; 606/181
[58] Field of Search .............................. 604/51, 118, 158, 604/164, 48, 111, 160, 166, 168, 264, 272, 900; 606/167, 181, 182

[56] References Cited

U.S. PATENT DOCUMENTS

| | | |
|---|---|---|
| 4,535,773 | 8/1985 | Yoon . |
| 4,944,724 | 7/1990 | Goldberg et al. ........................ 604/118 |
| 5,139,485 | 8/1992 | Smith et al. ............................. 604/158 |
| 5,352,206 | 10/1994 | Cushieri et al. ......................... 604/164 |
| 5,454,791 | 10/1995 | Tovey et al. ............................ 604/118 |
| 5,496,313 | 3/1996 | Gentalia et al. ......................... 606/34 |

*Primary Examiner*—Michael Buiz
*Assistant Examiner*—N. Kent Gring
*Attorney, Agent, or Firm*—Thomas C. Saitta

[57] ABSTRACT

A sleeve trocar having a coaxially mounted, spring biased internal obturator, where the obturator has one or more peripheral channels positioned around its periphery, the channels providing a gas flow path which allows gas to flow from the internal body cavity through the interior of the sleeve trocar and through a penetration indicator device, such that an audible sound is produced when the sleeve trocar has breached the internal cavity.

6 Claims, 2 Drawing Sheets

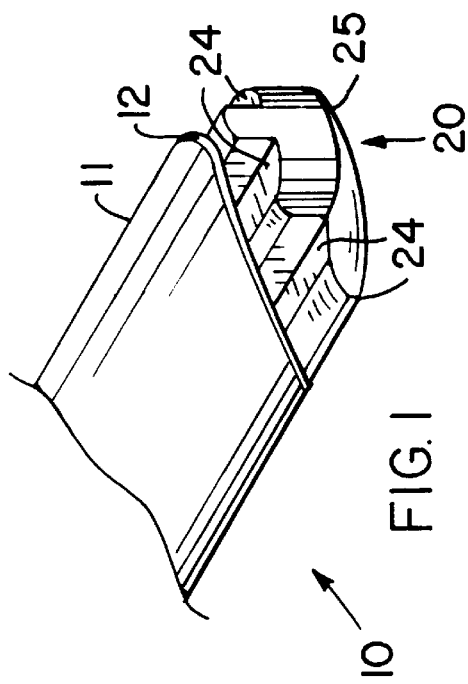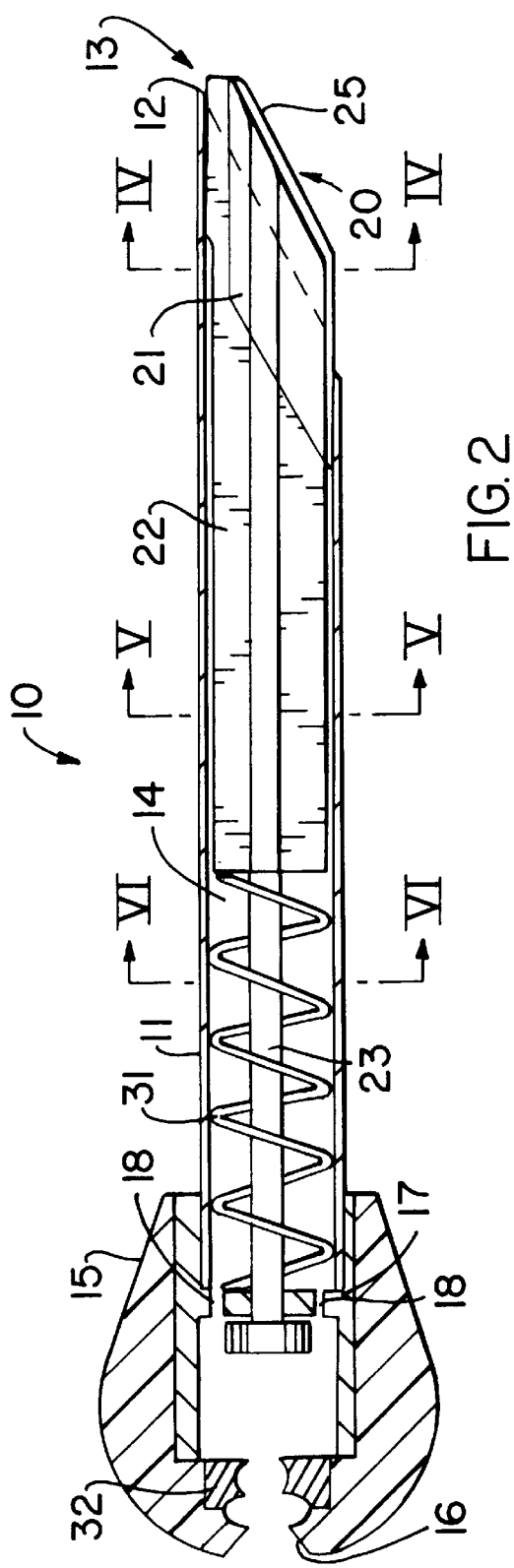

SLEEVE TROCAR WITH PENETRATION INDICATOR

BACKGROUND OF THE INVENTION

This invention relates generally to the field of body cavity piercing devices which are used in surgery to provide access to internal cavities through small puncture sites rather than large incisions. Such devices are generally known as trocars, and are constructed in one of two primary configurations. A standard trocar is a pointed rod, usually metal, which is designed to be contained within a blunt-tipped sleeve known as a cannula. The tissue puncture is made with the combination trocar and cannula, and the trocar is then removed from the cannula, which is left in place to provide an access conduit to the internal cavity. In the better design, a retractable sleeve is positioned about the trocar, the sleeve being biased such that it slides back to expose the tip of the trocar during insertion, but springs forward to cover the sharp point of the trocar once the internal cavity has been breached. The second style of trocar is similar in design to a Verress needle, which consists of a sharpened tubular needle with an internal blunt obturator provided with a passage for fluid, the internal obturator being spring biased so that it is forced into the body of the needle during the puncture step. The tubular needle itself punctures the tissue, while the obturator blocks the interior of the needle to prevent tissue from entering therein. The second style of trocar, which is also used in combination with a cannula, has a sharpened tubular member or sleeve containing a retractable obturator, the obturator being spring biased so that the tissue will push it some small distance into the sleeve during the puncture step. When the tip of the trocar reaches the internal cavity, which is usually inflated with a gas to provide an enlarged cavity, the biasing spring pushes the obturator forward past the sharp tip of the sleeve to prevent accidental puncturing or cutting of internal organs.

It is sometimes difficult for the surgeon to ascertain when the internal cavity has been breached by the trocar, as the only indication in standard trocars is a reduction in the amount of resistance felt by the surgeon, or the vibration or sound caused by the forward movement of the spring biased sleeve or obturator, once the trocar has entered the internal cavity. Various devices have been developed to provide an alternative indication of complete breach, either visually or audibly. Some devices use electrical components to produce audible or visible indications, for example U.S. Pat. No. 4,535,773 to Yoon or U.S. Pat. No. 5,496,313 to Gentalia et al., while others use the positive gas pressure in the internal cavity to fluctuate flexible members for a visual indication, U.S. Pat. No. 4,944,724 to Goldberg et al., or to generate sounds or move a visible indicator, U.S. Pat. No. 5,139,485 to Smith et al., U.S. Pat. No. 5,454,791 to Tovey et al., or U. S. Pat. No. 5,352,206 to Cushieri et al.

A major problem with the devices to date is that the passageways through either the solid trocar or the obturator in the sleeve trocar are easily susceptible to blockage by tissue during the insertion step. The known designs utilize small apertures connected to small bores, the bores opening into a larger region toward the proximal end of the trocar. The Cushieri et al. device, for example, uses a sharpened trocar inserted within a blunt cannula. An axially aligned bore of small diameter is made through each bevelled face forming the point, with the small bores opening into an enlarged internal chamber within the trocar body. The openings in the faces are very near the tip of the sharpened point, so that they directly encounter the tissue as the puncture is being made and are easily clogged. The device in Smith et al. is a Verress needle where the internal obturator has a small opening and bore, which by nature of the device must be relatively narrow and elongated since the needle is small in diameter and provides no space for an enlarged internal chamber. Thus the opening and bore can also easily become blocked during the insertion step.

It is an object of this invention to provide a trocar device which utilizes the positive gas pressure within an internal cavity to provide an audible or visual indication to the surgeon that the end of the trocar has penetrated into the cavity. It is a further object to provide such a device comprising a sleeve trocar with a biased obturator, where channels are positioned within the obturator head to allow gas to flow into the interior of the sleeve member and through an indicator device, such as a whistle. It is a further object to provide such a device where the flow channels are peripherally mounted on the obturator, such that one wall of each of the channels is formed by the interior of the sleeve member.

SUMMARY OF THE INVENTION

The invention is an improved sleeve trocar comprising a tubular sleeve member with a piercing tip containing a spring biased obturator with a blunt tip which extends slightly beyond the piercing tip except during the puncturing step. When the trocar is used to create an opening through the tissue into an internal cavity, the tissue encountered at the beginning of the puncturing step forces the obturator into the sleeve member, thereby exposing the piercing tip to cut through the tissue. When the piercing tip reaches the internal cavity, there is no longer any force against the blunt tip of the obturator and the spring forces the obturator back to the extended position, effectively shielding the piercing tip to prevent accidental puncturing or cutting of internal organs or the like. The improvement resides in providing the obturator head with a plural number of peripheral channels cut into the exterior of the obturator head, such that the channels are formed by the combination of the obturator head and the interior wall of the sleeve member. The channels extend the length of the obturator head and provide a flow path for gas from the internal cavity, the cavity having been previously inflated with the gas to produce a positive pressure and expand the cavity. When the piercing tip breaches the internal cavity, the gas flows through the peripheral channels into the relatively large open interior of the sleeve member, past the reduced obturator body and shaft and through one or more flow apertures to actuate a penetration indicator device, such as a whistle to produce an audible sound, mounted in the trocar handle. Because the channels are positioned peripherally rather internally on the obturator head, the likelihood of blockage during the puncturing step is significantly reduced. Should some tissue enter the channels during the puncturing step, the relative movement between the biased obturator head and the stationary sleeve member when the internal cavity is breached as the spring member forces the obturator into the extended position creates a shearing effect which will loosen any blockage in the channels, allowing the positive gas pressure to easily clear the channels such that sufficient air flow will reach the indicator mechanism.

BRIEF DESCRIPTION OF THE DRAWINGS

FIG. 1 is a partial perspective view of the piercing end of the sleeve trocar.

FIG. 2 is a view showing the sleeve trocar in cross-section with the obturator exposed.

DETAILED DESCRIPTION OF THE INVENTION

Figure 4:
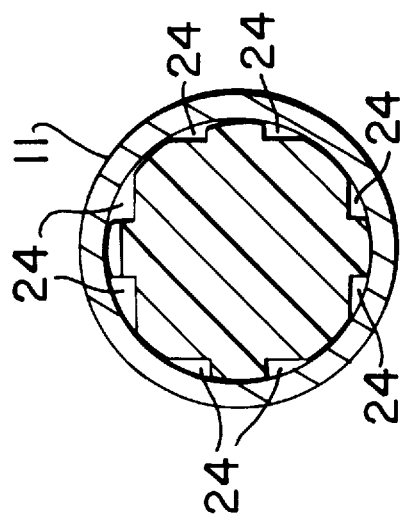
FIG. 4 is a cross-sectional view showing the obturator head in the sleeve member taken along line IV—IV of FIG. 2.

With reference to the drawings, the invention will now be described in detail with regard to the best mode and the preferred embodiment. The invention is an improved sleeve trocar, a trocar being a puncturing instrument used in surgery to provide a relatively small access opening through the outer tissue and muscle layers into an internal body cavity, the body cavity being inflated by the introduction of gas prior to use of the trocar. The trocar is coaxially aligned within a cannula, such that after the puncturing step the cannula is left in place and the trocar removed therefrom to provide an open conduit into the body cavity. A sleeve trocar comprises a hollow sleeve member with a sharpened end or tip which contains a coaxially mounted, spring biased obturator, the obturator being blunt tipped and extending beyond the piercing tip of the sleeve member unless forced into the sleeve member when body tissue is first encountered during the puncturing step. When the body cavity is breached, there is no longer any tissue to press the obturator into the sleeve member and the spring biasing member extends the blunt end of the obturator past the piercing end to prevent accidental puncturing or cutting by the sharpened end. In one type of sleeve trocar, gas flow apertures are provided in the obturator head such that when the body cavity is breached by the trocar the pressurized gas within the body cavity flows through the apertures and causes an audible or visible indicator to indicate to the surgeon that the cavity wall has been fully pierced. The invention improves on this known construction.

As seen in FIGS. 1 and 2, the invention is a sleeve trocar 10 comprising in general a sleeve member 11 containing a coaxially positioned, spring biased obturator 20 which in the passive position extends slightly beyond the open end 13 of the sleeve member 11. The sleeve member 11 is mounted into a handle member 15 having a general configuration which allows the surgeon to hold and press against handle 15 to insert the sleeve trocar 10 through the patient's tissue into the internal cavity. As shown, an insert member 17, generally H-shaped in cross-section, is provided to retain the sleeve member 11 and the shaft 23 of the obturator 20 in the handle 15. The handle 15 and insert member 17 are typically made of a polymer material, although it would also be possible to construct them out of metal. The sleeve member II is preferably constructed of metal, although it would also be possible to construct it out of a suitable polymer. The middle section of the insert member 17 is apertured to retain the obturator shaft 23 and determines the extent of distal travel, while also providing the back stop for the spring member 31 to apply distal biasing force against the obturator body 22 or head 21. The insert member 17 is provided with one or more flow apertures 18 through its middle section which provide means for gas to flow from the interior 14 of the sleeve member 11 into the handle 15 and through a penetration indicator means 32, such as an audible whistle, and finally out venting aperture 16. The open distal end 13 of sleeve member 11 is slanted relative to the central axis and is sharpened to create a piercing tip 12 for puncturing the body tissue.

Figure 6:
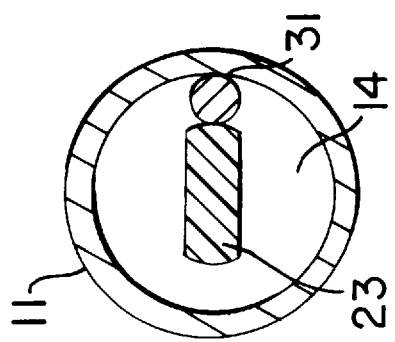
FIG. 6 is a cross-sectional view showing the obturator shaft in the sleeve member taken along line VI—VI of FIG. 2.

The obturator 20 is preferably formed of a polymer material, although it can be formed of metal as well. The outer diameter of the obturator head 21 is sized to correspond to the inner diameter of sleeve member 11, such that relative movement between the obturator 20 and the sleeve member 11 is in the axial direction only. As shown, the obturator 20 comprises obturator head member 21, obturator body member 22 and obturator shaft member 23. The obturator shaft 23 is sized to fit within a helical spring biasing member 31, as shown in FIGS. 2 and 6. The spring 31 pushes against the obturator body 22 as shown. Obturator body 22 provides a stepped transition between the obturator head 21 and obturator shaft 23, and allows obturator head 21 to be relatively short in axial distance as the obturator body 22 acts to maintain coaxial alignment with the sleeve member 11. Alternatively, obturator 20 could consist of a shaft 23 and head 21 only, such that spring 31 pushes directly against head 21. As seen in FIGS. 1 and 2, the length of the obturator 20 is such that a short portion of the obturator head 21 extends beyond the open end 13 of sleeve member 11 to shield piercing tip 12, such that the peripheral wall of obturator head 21 abuts the sharpened edge to prevent accidental cutting. The obturator head 21 is provided with a blunt tip 25 with a generally rounded configuration and slanted to correspond to the slant of the open end 13 of sleeve member 11.

Figure 5:
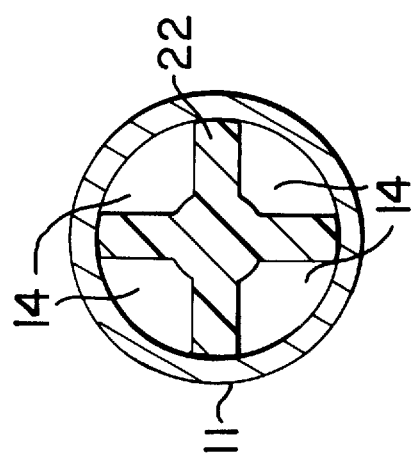
FIG. 5 is a cross-sectional view showing the obturator body in the sleeve member taken along line V—V of FIG. 2.
Figure 3:
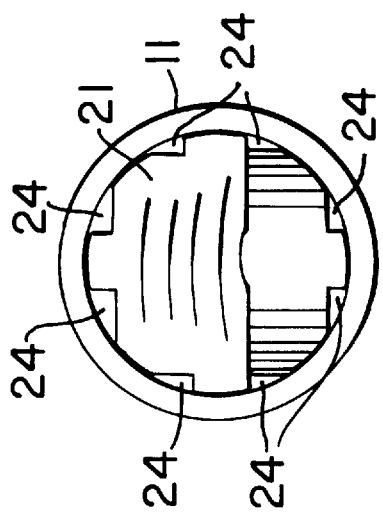
FIG. 3 is an end view of the piercing end of the device.

The obturator head 21 further comprises at least one and preferably a plural number of axial or longitudinally oriented peripheral channels 24. The peripheral channels 24 are cut into the exterior of the periphery of the obturator head 21 rather than through the interior. In this manner the flow path through the channels 24 is defined by the combination of the walls of the channel 24 inscribed in the obturator head 21 and the interior wall of the sleeve member 11. The peripheral channels 24 as shown in FIGS. 1 and 4 are rectilinear in cross-section, but they may be of any cross-sectional configuration such as semi-circular, ellipsoid, polygonal, etc. The peripheral channels 24 extend the full length of the obturator head 21 and open into the sleeve interior 14. The channels 24 may also expand or contract dimensionally over their length. Preferably, the obturator body 22 is configured with a much smaller cross-sectional area than the obturator head 21 and most preferably has a relatively minimal cross-sectional area in order to allow for unimpeded flow within the sleeve member 11, as shown in FIG. 5 where the obturator body 22 is configured as a cross. Obturator shaft 23 and spring member 31 are likewise preferably kept small in total volume, so that gas flow from the internal cavity through the peripheral channels 24 and sleeve interior 14 to flow apertures 18 is unimpeded. By positioning the channels 24 around the exterior periphery of the obturator head 21 and abutting the interior wall of sleeve member 11, there is less likelihood of the channels 24 being blocked by tissue during the puncturing step. Even more importantly, should tissue become lodged in the peripheral channels 24 during the puncturing step, the tissue will be partially dislodged by the distal movement of the obturator head 21 resulting from the biasing pressure of spring 31 after the internal cavity has been breached, allowing the positive gas pressure encountered in the internal cavity to easily clear the channels 24, allowing air to actuate the penetration indicator means 32 to provide an audible signal to the surgeon. Preferably, the vent aperture 16 and whistle 32 are generally coaxially aligned with the central axis of the sleeve trocar 10, such that the gas flow, and thus the audible sound, can be stopped by the surgeon pressing the palm of the hand over the vent aperture 16.

Although preferably the sleeve trocar 10 is constructed with an audible penetration indicator means 32, a visible indicator could be substituted, as such devices are will known in the art. For example, an inflatable member or free moving member could be positioned over the opening such that gas flow would extend it to provide a visual indication of gas flow into the sleeve trocar.

It is contemplated that equivalents and substitutions to the above elements and examples may be obvious to those skilled in the art. The true scope and definition of the invention therefore is to be as set forth in the following claims.

I claim:

1. In a sleeve trocar device for puncturing tissue to provide a conduit to an internal body cavity inflated by a gas, the sleeve trocar device comprising a spring biased obturator mounted coaxially within a sleeve member having a sharpened piercing tip, said obturator having a head with a blunt tip which extends beyond said piercing tip in the passive state and which is forced into said sleeve member to expose said piercing tip upon contact with tissue at the beginning of a puncturing step, said device further comprising penetration indicator means actuated by gas flow from said internal body cavity through said sleeve member which indicates when said internal body cavity has been breached by said piercing tip, and channel means in said obturator head which allows passage of gas from said internal body cavity through said obturator head and into said sleeve member to actuate said penetration indicator means, the improvement comprising:

locating said channel means around the periphery of said obturator head to form peripheral channels, said peripheral channels being defined by the combination of the interior wall of said sleeve member and the walls of said channel means cut into the periphery of said obturator head.

2. The device of claim 1, where said peripheral channels are coaxially aligned with said obturator and said sleeve member.

3. The device of claim 1, where said penetration indicator means is an audible device.

4. The device of claim 1, where said device further comprises a handle and said penetration indicator means is positioned in said handle.

5. The device of claim 1, where said obturator further comprises a body having a smaller cross-sectional area than said obturator head.

6. The device of claim 1, where said channel means cut into said obturator head are rectilinear.

* * * * *